United States Patent [19]
Fleming

[11] Patent Number: 6,082,855
[45] Date of Patent: Jul. 4, 2000

[54] EARPLUG ATTACHMENT FOR EYEGLASSES

[75] Inventor: Thomas Fleming, San Diego, Calif.

[73] Assignee: Bacou USA Safety, Inc., San Diego, Calif.

[21] Appl. No.: 09/394,213

[22] Filed: Sep. 10, 1999

Related U.S. Application Data

[60] Provisional application No. 60/100,621, Sep. 16, 1998.

[51] Int. Cl.$^7$ ........................................................ G02C 5/20
[52] U.S. Cl. ................................................ 351/123; 351/158
[58] Field of Search ........................... 351/158, 41, 121, 351/111, 123; 128/864, 857; 602/24

[56] References Cited

U.S. PATENT DOCUMENTS

| | | | |
|---|---|---|---|
| 5,717,479 | 2/1998 | Rickards | 351/158 |
| 5,781,272 | 7/1998 | Bright et al. | 381/123 |

*Primary Examiner*—Hung Xuan Dang
*Attorney, Agent, or Firm*—Freilich, Hornbaker & Rosen

[57] ABSTRACT

An attachment (10) for safety eyeglasses includes a mount (30) that mounts on an eyeglass temple bar, an earplug (32) that can fit into the ear canal to block noise, and a coupling (34) that connects the mount to the earplug. The mount includes a tube of elastomeric material that can be stretched over the temple bar to fix its position and prevent "jiggling". The coupling includes a wire of resilient plastic that is wound into a tight helix. The diameter of the helix is about 1 cm, which allows it to be stored between the rear of the outer ear and the skull, to minimize earplug motion when the earplug is not inserted into the ear canal.

12 Claims, 3 Drawing Sheets

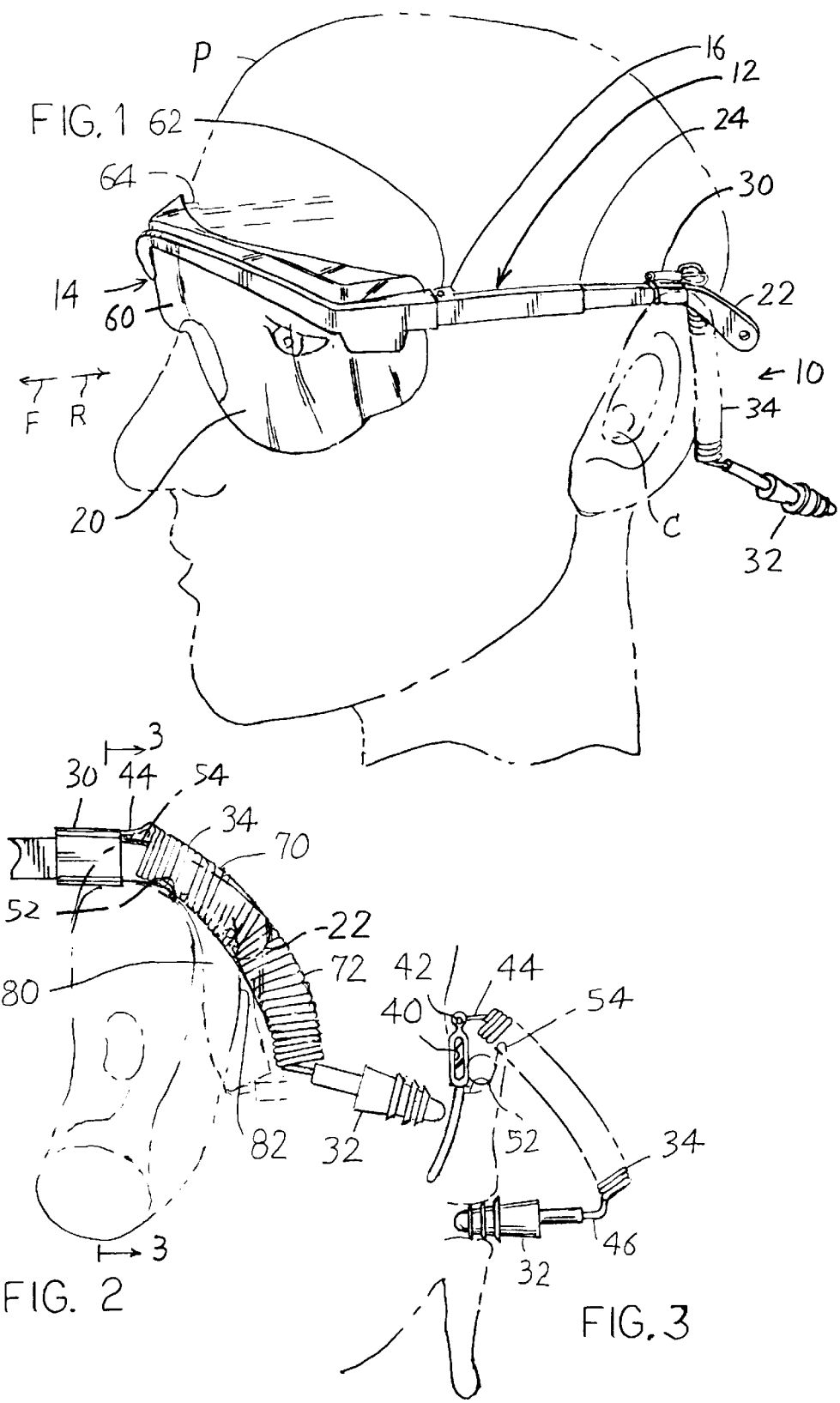

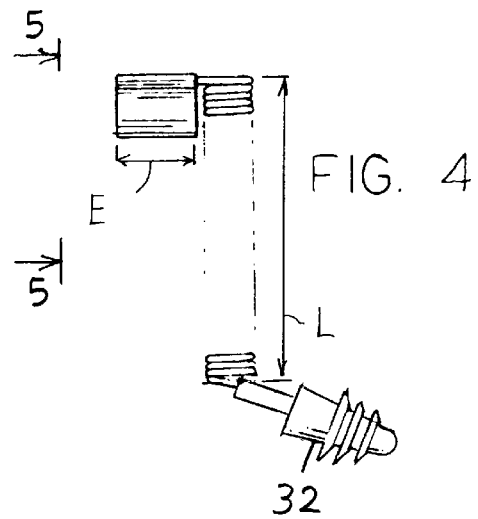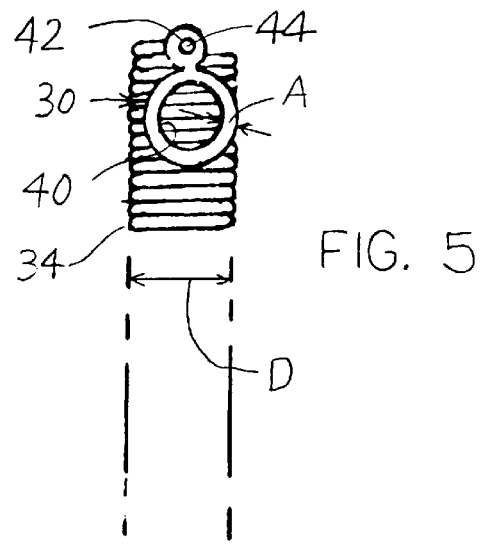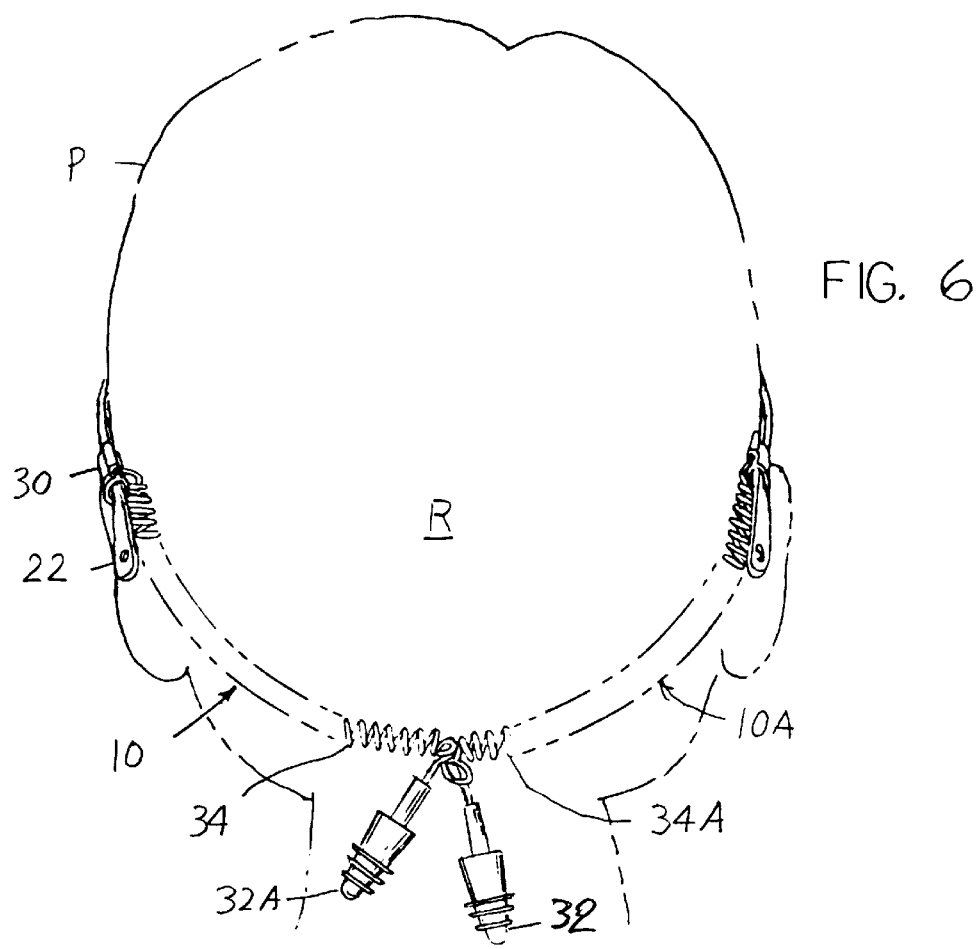

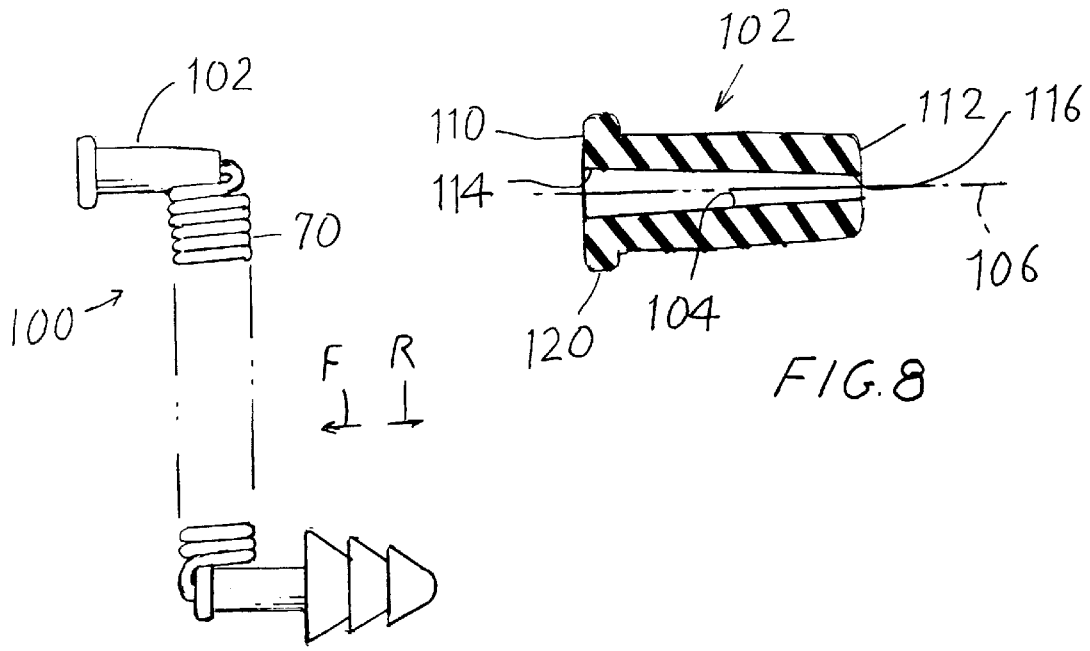
FIG. 7
FIG. 8
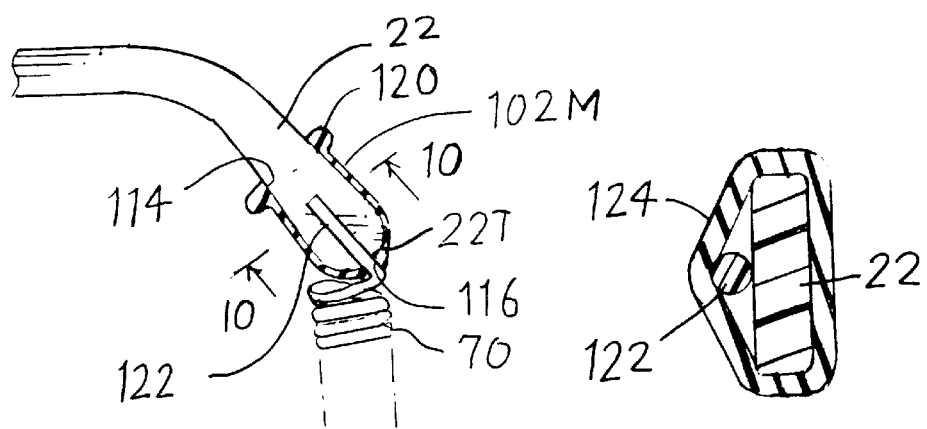
FIG. 9
FIG. 10

EARPLUG ATTACHMENT FOR EYEGLASSES

CROSS-REFERENCE

Applicant claims that the benefit of Provisional Application Ser. No. 60/100,621 filed Sep. 16, 1998.

BACKGROUND OF THE INVENTION

This invention relates to an attachment that mounts on the temple bar of a safety eyeglass and that holds a noise-blocking earplug so it can be plugged into the ear canal whenever the environmental noise level becomes high.

There are many manufacturing and research environments where the eyes of a worker must be protected by a safety eyeglass, and where the ears of the worker must sometimes be protected against very loud noises. When the noise level is not high, workers often wish to remove the earplugs from the ears, to allow them to better hear sounds and to avoid the discomfort of earplugs in their ears. The earplugs can be entirely separate items, although this requires a worker to store the earplugs when not used, which can be inconvenient. The earplugs can be attached to a device that supports them on the temple bars of the eyeglass, so the earplugs are very conveniently available when they must be again plugged into the ear canal, and so they can be easily stowed when not used. U.S. Pat. No. 262,491 shows such an assembly, where a one-piece device includes a strap forming a loop at one end that can be looped about the temple bar, and forming an earplug at the opposite end. Although such a device can conveniently store an earplug, it would be desirable to provide an attachment that enables storage of an earplug as comfortably and conveniently as possible with minimum "jiggling" of the earplug as the worker moved his/her head, while enabling insertion into the ear canal with maximum comfort.

SUMMARY OF THE INVENTION

In accordance with one embodiment of the present invention, an attachment apparatus is provided that includes a mount that mounts on an eyeglass temple bar, an earplug that can be inserted into the ear canal, and a coupling that couples the mount to the earplug. The attachment enables convenient and substantially rattle-free storage of the attachment when the earplug is not in use. The coupling includes a wire that is wound into a helix, with one end connected to the mount and the other end connected to the earplug. The wire is preferably a resilient polymer and is preferably wound into a tight helix wherein adjacent terms of the helix substantially abut one another. The diameter of the helix is preferably about one centimeter, to facilitate jiggle-free mounting in the gap between the rear of the outer ear and the skull of the wearer.

The mount is preferably formed of an elastomeric tube which has been stretched to fit over the temple bar end. This results in rattle-free mounting. One simple mount includes a tube of elastomeric material with most of its length stretched over the rear end of the temple bar, and with an end of the coupling wire extending through a hole at the rear of the tube. The wire end is pressed between the stretched tube and the temple bar. The tube preferably has a flange on the outside of its front end to facilitate mounting on the temple bar and removal therefrom. Another simple mount has two integral tubes, including one that can be stretched over the temple bar and another constructed to receive an end of the wire.

The novel features of the invention are set forth with particularity in the appended claims. The invention will be best understood from the following description when read in conjunction with the accompanying drawings.

BRIEF DESCRIPTION OF DRAWINGS

FIG. 1 is an isometric view of a combination of a safety eyeglass and of an earplug attachment, and showing the combination mounted on the head of a person who is shown in phantom lines.

FIG. 2 is a partial side elevation view showing the rear portion of a temple bar and the attachment of FIG. 1 shown mounted on a wearer's ear, the ear being shown in phantom lines and the coupling of the attachment being shown in phantom lines in a rattle-free position in a gap between the outer ear of the wearer and the wearer's skull.

FIG. 3 is a view taken on line 3—3 of FIG. 2, and with the ear plug inserted into the ear canal of the wearer.

FIG. 4 is a side elevation view of only the attachment of FIG. 1.

FIG. 5 is an enlarged view taken on line 5—5 of FIG. 4.

FIG. 6 is a rear elevation view of the person and combination of FIG. 1, showing the attachments stretched and looped to hold them against jiggling.

FIG. 7 is a side elevation view of an attachment constructed in accordance with another embodiment of the invention.

FIG. 8 is a sectional view of only the mount of the attachment of FIG. 8.

FIG. 9 is a partial sectional view of the attachment of FIG. 7 and of a portion of a temple bar, showing the mount and an end of the coupling wire mounted on the temple bar.

FIG. 10 is a sectional view taken on line 10—10 of FIG. 9.

DESCRIPTION OF A PREFERRED EMBODIMENTS

FIG. 1 illustrates an attachment 10 of the present invention, which is mounted on one of a pair of temple bars 12 of a safety eyeglass 14 that is worn by a person. The safety eyeglass has a front part 60 forming an eye shield 20 with transparent viewing areas (that can be tinted for protection against sun-light or welding light). The eyeglass has left and right sides 62, 64, with a forward end 16 of each temple bar being pivotally attached about a vertical axis to one side of the eye shield. The temple bar has a rear end 22 that is enlarged in width and that is curved to extend at a slight downward incline to fit on the ear. A temple bar middle 24 connects its opposite ends. The attachment 10 includes a mount 30 that mounts on the temple bar, a noise-blocking earplug 32 for insertion into the ear canal C when needed, and a coupling 34 that connects the mount 30 to the earplug 32.

As shown in FIGS. 2 and 3, the coupling 34 is preferably in the form of a helical coil 70 of a resilient wire 72 of solid polymer, such as polyurethane. The mount 30 is formed from an elastomeric material having a Shore hardness that is preferably less than 50, to easily stretch and provide high friction against the polyurethane wire. The mount is formed with two holes, including a large hole 40 for receiving the temple bar and a small hole 42. A wire inner end 44 extending from one end of the coil, lies in the mount hole 42. An opposite wire outer end 36 extends from the opposite end of the coil into the rear of the earplug 32 and may be held therein by adhesive.

FIG. 5 shows the elastomeric mount 30 as it is initially formed, with round holes 40, 42. Applicant finds that the straight wire end 44 can be inserted into the smaller hole 42 by merely forcing the wire end into the hole. The wire end 44 has a larger outside diameter than the initial diameter of the small hole 42. This results in an interference fit between the polyurethane wire and the high friction elastomeric material of the mount, along the length of the hole (which is a plurality of times greater than its diameter), which results in secure holding of the wire in the hole 42. The walls of the large hole 40 are readily elastically deformed to slip over the enlarged temple bar 22 and to closely hold itself onto the temple bar without jiggling around, for temple bars of a variety of widths and thicknesses.

One common way in which the attachment is worn is as shown FIG. 2, with a coil extending down and rearwardly from the mount 30. Both the temple bar end 22 and the coil 70 lie against the area of the person's ear which forms a shelf 52 that connects the top 54 of the outer ear (pinna) to the rest of the head (the skull). The ear plug 32 can be inserted into the ear canal as shown in FIG. 3, by flexing of the coil, without noticeable sideward forces of the earplug 32 against the ear canal, which would lead to discomfort. All of this is accomplished with a coil 34 of only moderate length, because of the high flexibility of the coil in bending in any direction to reach the ear canal. It is also possible to slide the mount 36 forward so the earplug lies over the ear canal and can be quickly inserted therein.

When the coil is in the position shown in solid lines in FIG. 2, the lower portion of the coil can "jiggle" slightly, causing even greater jiggling of the ear plug 32, which can be annoying to the wearer. FIG. 6 shows one technique which applicant has found to be useful in holding a pair of attachments 10, 10A when the earplugs 32, 32A are not in the wearer's ear canals. Coils 34, 34A are extended behind the rear R of the person's head, and one of the earplugs is wrapped about 180 degrees around the coil wire end of the other attachment. The coils 34, 34A are maintained under tension because they are stretched, which avoids dangling earplugs that are felt to move up and down as the wearer moves his or her head. Each of the coils is stretched by about 50% to 100% of its initial length. The fact that each of the couplings formed by the coils is resiliently stretchable by at least 50% of its length, enables the mounting technique of FIG. 6.

In an attachment of a construction illustrated, that applicant has made, the mount 30 was formed of a thermoplastic rubber, with a Shore hardness of 35. The mount had a wall thickness A (FIG. 5) of 1 mm, a length E of 5.5 mm, a large hole 40 that was cylindrical and of a diameter of 5.5 mm, and a small hole 42 that was cylindrical and that had a diameter of 1.5 mm. The coil 70 was formed of a wire of urethane with a wire having a round cross section and a diameter 1.8 mm. The coil had a coil outside diameter D of 9 mm and had twenty-six turns that resulted in an unstretched length L of 45 mm (1¾ inches).

Applicant has found that with a coil 70 (FIG. 2) having a diameter of about 9 mm, the lower half of the coil can be pushed forward into the gap 80 that lies between the rear 82 of the outer ear at its upper half, and the skull of the wearer, and remains there. A person can put on the eyeglasses with the attachments lying in the position shown in solid lines in FIG. 2, and with the lower half of the coil pushed forward into the gap 80. The fact that the coil is of a polymer results in a low thermal conductivity. This is a convenient way to minimize jiggling of the ear plug. It enables rapid use of the ear plug by merely pulling the coil out of the gap 80 between the ear and skull, and inserting the earplug into the ear canal. A coil diameter of up to almost 2 cm will remain in the gap 80 and a coil diameter of much less than 9 mm will remain in the position shown in solid lines in FIG. 2, but will not remain pressed in place in the gap 80. A coil diameter of about 1 cm (8 mm to 16 mm) is preferred. The diameter of the helix can vary along its length, although a helix of constant diameter is preferred. A helical coil of at least 10 turns is preferred.

FIGS. 7–10 illustrate another attachment 100 forming an apparatus for holding an earplug on a temple bar. The attachment includes a temple bar mount 102 in the form of a tube of elastomeric material. As shown in FIG. 8, the tube has a through passage 104 that extends along an axis 106 of the tube between front and rear ends 110, 112 of the tube. The passage has a large front end hole 114 and a smaller rear end hole 116. The coil 70 and earplug 32 may be the same as the first embodiment.

FIG. 9 shows how the mount at 102M is mounted on a temple bar rear end 22. The mount is expanded over the temple bar by elastic stretching of the mount, resulting in high friction holding of the mount to the temple bar. The mount has a flange 120 at its front end, which helps to push the tubular mount onto the temple bar. This is accomplished by placing the front end hole 114 of the elastic tube against the extreme rear tip 22T of the temple bar, and pushing the flange 120 forwardly, as by alternately pushing the top and bottom of the flange forwardly until the position of FIG. 9 is achieved. Prior to installing the elastic tube mount on to the temple bar, the wire end 122 of the coil 70 has been inserted through the rear end hole 116 of the tube. As a result, when the elastic tube is in place the wire end 122 is compressed, as shown in FIG. 10, between the elastic tube side walls 124 and the temple bar 22. This results in a resistance to pullout, which is sufficient to prevent loss of the coil during normal usage. While the diameter of the wire at 122 is about 1.8 mm, the diameter of the rear end hole 116 in the elastic tube is about 1.5 mm, for a moderate interference fit therewith.

Thus, the invention provides an ear plug attachment for mounting on the temple bar of an eyeglass, where the attachment is of relatively short length to minimize annoyance when the earplug dangles at the end of the attachment, and which enables the earplug to easily reach the ear canal. The attachment includes a mount for mounting on a temple bar, which is preferably an elastic tube for tightly gripping the temple bar to avoid rattling. A coupling that connects the mount to the ear plug, includes a helical coil of wire, with the coil preferably being tightly wound so adjacent turns of the coil lie against each other (are spaced by less than the diameter of the wire). The coil is preferably of a polymer material which has low heat conductivity to avoid the feeling of something that is cold or hot touching the ear of the wearer when the attachment is first put on the wearer. The coil is preferably of about 1 cm diameter, so it can be pressed into the gap between the upper rear part of the outer ear and the skull of the wearer and remains there. The mount can be constructed of an elastomeric tube with an outer flange at its front end, to facilitate pushing the elastic tube onto the end of the temple bar. An end of the coil can be held by being pressed between the stretched tube and the temple bar.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for use with an eyeglass that includes a front part with left and right sides and transparent viewing areas for lying over a wearer's eyes, and that includes a pair of temple bars that each extends rearwardly from one of said sides and that each has a rear end for lying on the outer ear of the wearer, comprising:

a temple bar mount that is mountable on one of said temple bars;

an earplug that can fit into an ear canal to block sound; and a coupling that connects said mount to said earplug;

said coupling comprising a resilient wire that is wound into a multi-turn helix.

2. The apparatus described in claim 1 wherein:

the outside diameter of said helix is about one centimeter, whereby said helix can be held in place in the gap between the upper rear part of the outer ear and the skull.

3. The apparatus described in claim 1 wherein:

said mount comprises a tube of elastomeric material having a passage forming a first end hole of a first diameter to tightly surround and hold to a temple bar rear end, with said passage having a smaller second end hole with an end of said wire projecting through said second end hole.

4. The apparatus described in claim 1 wherein:

said mount comprises a tube of elastomeric material with an outside, and with a flange on said outside of a first end of said tube which forms said first end hole.

5. The apparatus described in claim 1 wherein:

said mount includes two integral tubes with parallel but spaced axes, with one tube constructed to be stretched over one of said temple bars and the other constructed to tightly receive an end of said wire.

6. The apparatus described in claim 1 wherein:

said wire is formed of a resilient polymer and has a wire diameter of about 2 mm.

7. The combination of an eyeglass that has a front part with transparent opposite side areas and a pair of temple bars that extend from opposite sides of said front part and that have rear ends for lying between the top of the outer ear and the skull of a wearer, and a pair of atachments that each includes a mount for mounting on a temple bar, an earplug for insertion into an ear canal, and a coupling that connects said mount to said earplug wherein:

each of said couplings includes a resilient plastic wire that is wound into a tight helix of more than 10 turns, and that has an outer helix diameter of about one centimeter.

8. The combination described in claim 7 wherein:

said mount comprises two tubes with integral tube walls and spaced tube axes, with the walls of one tube being stretched over one of said temple bars and the walls of the other receiving an end of said wire in an interference fit.

9. The combination described in claim 7 wherein:

said mount is in the form of a tube of elastic material with a front end having a flange on the outside of the tube, to thereby facilitate pushing the front end onto a temple bar rear end.

10. The combination described in claim 7 wherein:

said mount is in the form of a tube of elastomeric material having a through passage extending along an axis, with said passage having a front end where said tube is stretched around said temple bar and with said passage having a rear end with said wire projecting into said passage through said passage rear end, with said wire having a wire end lying in said passage and pressed between the stretched tube and the temple bar.

11. Apparatus for use with an eyeglass that includes a front part that has left and right sides and that has transparent viewing areas for lying over a wearer's eyes, where the eyeglass includes a pair of temple bars that each extends rearwardly from one of said sides and that has a rear end for lying on the outer ear of the wearer, comprising:

a temple bar mount that is mountable on one of said temple bars;

an earplug that can fit into an ear canal to block sound; and a coupling that connects said mount to said earplug;

said temple bar mount comprises a tube of elastomeric material having a front end and having a passage, said tube having an outside, and said tube front end having a flange on its outside.

12. The apparatus described in claim 11 including said eyeglass, and wherein:

said coupling comprises a wire wound into a helix;

said tube has a rear end and said passage is a through passage that extends through said tube rear end;

said tube front end is stretched around the rear end of one of said temple bars, and said wire has a front end that projects into said passage through the rear end of said tube, and that is pressed between said stretched tube and said one of said temple bars.

* * * * *